United States Patent [19]
Torger

[11] Patent Number: 5,687,741
[45] Date of Patent: Nov. 18, 1997

[54] GARMENT FOR RELEASABLY SECURING CONDOMS

[76] Inventor: Karin S. Torger, 15 Hermann #606, San Francisco, Calif. 94102

[21] Appl. No.: 739,031

[22] Filed: Oct. 28, 1996

Related U.S. Application Data

[63] Continuation-in-part of Ser. No. 602,001, Feb. 15, 1996, abandoned.

[51] Int. Cl.$^6$ .................................................. A61F 6/02
[52] U.S. Cl. ........................................ 128/842; 604/353
[58] Field of Search ................................. 128/842, 844, 128/918; 604/347–353

[56] References Cited

U.S. PATENT DOCUMENTS

| | | | |
|---|---|---|---|
| 2,591,783 | 4/1952 | Craddock | 604/353 |
| 4,664,104 | 5/1987 | Jaicks | 604/353 |
| 4,942,885 | 7/1990 | Davis | 128/842 |
| 5,181,527 | 1/1993 | Dorsey | 128/844 |
| 5,269,320 | 12/1993 | Hunnicutt | 128/842 |
| 5,535,757 | 7/1996 | Fleming, Jr. | |

OTHER PUBLICATIONS

Reality® Female Condom, Female Health Division, Wisconsin Pharmaceutical Co., Chicago, IL (undated brochure).

*Primary Examiner*—Michael A. Brown
*Attorney, Agent, or Firm*—Douglas E. White; Acronational Law Firm

[57] ABSTRACT

A woman's panty-type undergarment provides a means of attaching a releasable, securable, and disposable female condom that can be comfortably worn for hours before anticipated intercourse, thereby providing a barrier to the entrance of male sperm and bodily fluids which may cause pregnancy or spreading of diseases such as AIDS. A resilient ovoid condom attachment member is sewn or otherwise attached to an opening in the crotch portion of the panty. The female condom is inserted into the wearer's vaginal opening and then the outer ring of the female condom is threaded through a slit aperture in the ovoid member and stretched over a circumferential head flange, whereby it is secured around a narrow annular neck that is disposed between a base plate of the attachment member and the head flange.

15 Claims, 8 Drawing Sheets

GARMENT FOR RELEASABLY SECURING CONDOMS

CROSS REFERENCE TO RELATED APPLICATIONS

This application is a continuation in part of U.S. application Ser. No. 08/602,001, filed Feb. 15, 1996, abandoned.

FIELD OF THE INVENTION

The present invention relates generally to a coital protective garment that is useful during sexual activity in preventing the transmission of disease-producing organisms and fertilizing spermatozoa. Specifically, it relates to a woman's undergarment which accommodates a releasably secured female condom that is easy to use, comfortable, visually appealing and does not require disruptive activity immediately before sexual intercourse.

BACKGROUND OF THE INVENTION

Male condoms are known and have been available for centuries. Most recently, male condoms have become widely available which are made of a thin latex material. Much attention has been drawn to the fact that many times people do not choose to use condoms for protection from pregnancy and sexually transmitted diseases. Much attention has also been drawn to the fact that, for a variety of reasons, including the emotional frenzy of the moment or the lack of prudent thinking due to excess alcohol or the like, sexual partners do not want to take the time and effort to put a conventional condom on the male.

Female condoms are also known, such as the REALITY Female Condom manufactured by Chartex International of London, England, and distributed in the U.S.A. by Wisconsin Pharmaceutical Company of Chicago, IL (U.S. Pat. No. 4,735,621). These condoms are inherently larger in diameter than the standard male condom. They also contain a removable resilient free inner ring which holds the condom in place at its base once inserted. The act of correctly inserting the female condom is somewhat time-consuming. Such interruption can diminish the spontaneity of the moment of sexual arousal. The female condom can be inserted into the vagina at an earlier time, such as several hours before presumed sexual activity is to begin. However, there is no guarantee that the female condom will stay in its optimal position. Furthermore, once intercourse begins, the outermost upper rim of the female condom may accidentally be pushed into the vagina by the penis as it enters the vagina, thereby defeating the purpose of the condom.

Other female undergarments incorporating prophylactics for the purpose of preventing pregnancy and sexually transmitted diseases have been proposed in prior patents and will be discussed at this time. However, as it will be shown, none of the previous designs teach the optimal combination of features which are the object of the present invention.

U.S. Pat. No. 4,664,104 by Jaicks describes an anti-herpes modality system in which a removable condom is attached to a panty made of non-breathable material. The shape of the ring which holds the condom is round. This would make it quite uncomfortable for a woman to wear for extended periods of time before intercourse. The means of holding the condom is minimal and, with normal pressures of intercourse, could disengage. Additionally, the non-breathable nature of the panty material also would make it very uncomfortable for a woman to wear such a garment for any extended period of time, such as several hours before intercourse. The intent of the invention is to have the male partner put on the condom portion and then to have the penis enter the female and then to manually lock the open end of the condom to the ring located on the female panty. This activity is likely to take the spontaneity out of sexual intercourse. Finally, the action of the penis moving in and out of the vagina would cause the tight fitting condom to alternately roll on and off the base of the penis with each penetration, causing discomfort to the male partner.

U.S. Pat. No. 4,834,114 by Borman shows a contraceptive system having a one-piece formation to be worn by males and females. It includes an integral triangular-shaped shield, to each end of which shield straps are attached. The straps are tied around the person's torso to hold the shield in place. The tubular portion is described as thick-walled at the bottom. Since the entire unit is made of one piece and is of significant complexity and cost, it would seem that it is not a disposable unit. This would also make it necessary to clean the unit after each use. Additionally, the opening of the unit is round and maintained in a round configuration by tension resulting from the attached straps. Since the normal configuration at the entrance of the vagina is a closed slit configuration, the forced round shape would become uncomfortable quickly. Finally, the non-breathable triangular shield would also cause sweating and discomfort after a short period of time.

U.S. Pat. No. 4,637,078 by Southwell teaches a panty-styled undergarment designed for the handicapped which includes a removable panel which exposes the vagina. It was not designed with the idea of having intercourse and provides no contraceptive protection and therefore does not contain the unique combination of elements as will be described in the present invention.

U.S. Pat. No. 4,862,901 by Green, U.S. Pat. No. 5,269,320 by Hunnicutt, and U.S. Pat. No. 5,181,527 by Dorsey each describe a panty in which a liquid impervious panel is integral to the lower portion of the panty. The panel includes a collapsed tubular portion which is supposed to expand outward when a penis enters the vaginal area. This action, in practice, would be difficult to accomplish because the penis would cause the prophylactic either to dislodge from the vagina (since there is no inner retaining ring to hold the female condom in place) or to become torn from the force of the penis attempting to push the condom into place.

Additionally, the entire panty and condom must be cleaned after each use. Finally, the manufacture of a collapsible condom of the manner described in these patents could be difficult and would necessitate the use of a relatively heavy wall of latex or comparable material, thereby reducing the sensory contact between the male and female partner and causing reduced pleasure during sexual intercourse.

U.S. Pat. No. 4,834,113 by Ready proposes a rolled, rather than a telescoped, portion forming an integral condom attached to a non-breathable undergarment. While the rolled configuration may cause easier deployment as the penis enters the vagina, all the other features, including non-breathable material and the need to clean the entire garment after each use prove problematic for the intended use. Additionally, none of the above patents show a female undergarment that is of a pleasing appearance when the condom feature is not in use. This can have a negative effect on the mood of the male partner during the period before sexual intercourse occurs.

SUMMARY OF THE INVENTION

A garment, preferably quality lingerie underpants, and possibly other garments, is comprised chiefly of breathable sewn fabric. It has a central opening in its crotch area to which is affixed an ovoid (oval-shaped) condom attachment member with which to releasably secure female condoms. The base panel of the ovoid member is sewn into or otherwise bound to the fabric of the crotch of the panty. Rising up from the base is a protruding head having a narrow neck. A circumferential flange projects radially outward laterally from the head, which head surrounds a slit-like aperture.

The film tube of the female condom is inserted into the wearer's vaginal opening and retained therein by its lower free inner positioning ring. The outer upper rim ring of the condom then is threaded through the center aperture of the ovoid member and stretched over the upper circumferential flange of the head of the ovoid member. The rim ring of the female condom snaps under to rest in the groove or neck under the circumferential head flange.

The ovoid member uses its shape to hook the outer upper rim ring of the female condom: first at the bottom and top protuberances of the circumferential flange of the projecting head of the attachment member; and then along the groove forming the narrowed neck underneath said flange to hook entire condom rim ring. Finally, one of several different possible securing mechanisms at the sides of the ovoid member secures the rim ring from being pulled off during intercourse by pressure.

After the condom is inserted and attached to the ovoid member on the panty, a fabric panel or flap is folded up and over the crotch area and attachment member. A free end of the flap may be releasably attached to the panty by hook and loop fastener material, such as VELCRO. The base end of the flap may be held onto the panty by snaps or the like so that the entire flap may be removed, if desired.

This allows the woman to wear the condom comfortably and discreetly for hours ahead of time. She then is protected from sexually transmitted disease and is ready for spontaneous intercourse at a moment's notice.

There is an optional small pocket on the front of the panty with which to hold a lubrication packet, so it is handy when needed. This packet quickly becomes warmed by body temperature. This makes it more comfortable to apply.

FEATURES AND ADVANTAGES

It is an object of the present invention to provide an attractive woman's panty-type undergarment which provides a means of attaching a releasable, securable, and disposable female condom. The condom can be comfortably worn for hours before anticipated intercourse, thereby providing a barrier to the entrance of male sperm and bodily fluids which may cause pregnancy or spreading of diseases such as AIDS.

It is an object of the present invention to provide such an undergarment in which no time-consuming actions are required to prepare for protected sexual intercourse during the excitement of sexual arousal just prior to intercourse.

It is an object to provide such an undergarment in which the panty material is made of comfortable, breathable material.

It is further object of the present invention to provide such an undergarment in which the secured condom is in a vaginally inserted yet collapsed condition, thereby enabling the user to comfortably wear the condom for hours.

It is a further object of the present invention to provide such an undergarment wherein the outer lip or rim ring of the female condom is easily secured to a resilient ovoid condom attachment member located at the crotch area of the panty.

Yet a further object is to provide such an undergarment wherein a breathable fabric flap, which matches the rest of the panty, covers the condom area until sexual intercourse is ready to commence.

It is a further object of the present invention to provide such an undergarment where a pocket or pockets of matching panty fabric are sewn onto the panty for the purpose of holding prepackaged containers of lubricant, extra condoms, and the like.

Still a further object is to teach a device that is reusable, i.e., the condom may be replaced repeatedly without having to discard the panty or the integral ovoid member. Furthermore, the panty of the present invention may be removed for urination without having to dislodge the condom from the vagina.

An important object is to teach a garment device that covers the entire pubic area during intercourse, for added protection against HIV and other sexually transmitted diseases.

Accordingly, a feature of the invention is a garment apparatus for releasably securing female condoms including: a panty made of breathable material, the panty having a crotch, the crotch having an opening; and a resilient ovoid member affixed to the panty at the crotch opening, the ovoid member having: a base panel; an annular ovoid neck protruding up from the base panel; and a circumferential head flange on an upper end of the neck projecting radially outward laterally from the neck, the neck and head flange forming a central slit-shaped aperture, the aperture communicating with the opening.

Another feature is the panty material may be cloth fabric, the ovoid member may be plastic, and the ovoid member may be sewn onto the crotch.

Another feature is a plurality of horizontally disposed resilient flange protuberances radially projecting from the head flange, which protuberances vary the effective width of the head flange.

Still another feature of one embodiment of the invention is at least one retaining bar protruding up from the base panel, the retaining bar disposed radially outward of the neck and positioned closely adjacent thereto.

A useful optional feature includes a pair of such retaining bars, the retaining bars being diametrically opposed on opposite sides of the neck.

A feature is a releasable cloth flap portion on the crotch, which flap covers the ovoid member Yet another feature is the apparatus may include hook and loop type fasteners securing a top of the flap to the panty.

One other optional feature is at least one pocket affixed to the panty.

Another feature is an apparatus that is easy to use, attractive in appearance and suitable for mass production at relatively low cost.

Other novel features which are characteristic of the invention, as to organization and method of operation, together with further objects and advantages thereof will be better understood from the following description considered in connection with the accompanying drawing, in which a preferred embodiment of the invention is illustrated by way of example. It is to be expressly understood, however, that the drawing is for illustration and description only and is not intended as a definition of the limits of the invention.

Certain terminology and derivations thereof may be used in the following description for convenience in reference only, and will not be limiting. For example, words such as "upwardly," "downwardly," "leeward," and "rightward" would refer to directions in the drawings to which reference is made unless otherwise stated. Similarly, words such as "inwardly" and "outwardly" would refer to directions toward and away from, respectively, the geometric center of a device or area and designated parts thereof. References in the singular tense include the plural, and vice versa, unless otherwise noted.

Figure 1:
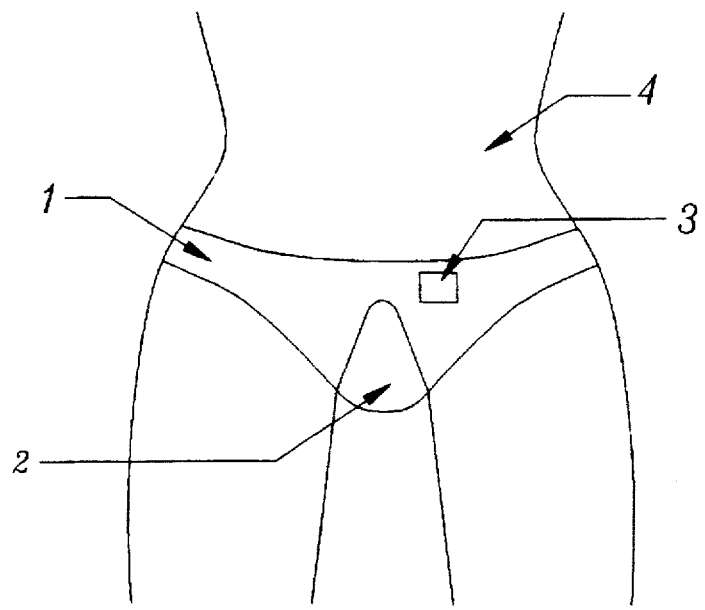
FIG. 1 is a front view of a user wearing the female condom securing garment or device of the present invention.

DRAWING REFERENCE NUMERALS 1 garment
2 flap
3 pocket
4 user
5 hook and loop fastener
6 ovoid member
7 hook and loop fastener
8 female condom
9 opening
10 free ring
11 film robe
40 snaps
102 hole
104 protuberance
106 protuberance
107 protuberance
108 retaining bar
110 retaining bar
112 protuberance
114 protuberance
116 protuberance
118 protuberance
120 protuberance
122 rim ring
130 aperture
132 base panel
134 neck
136 head
138 circumferential head flange
206 ovoid member
2104 protuberance
2106 protuberance
2107 protuberance
2112 protuberance
2114 protuberance
2116 protuberance
2118 protuberance
2120 protuberance
2130 aperture
2132 base panel
2134 neck
2136 head
2138 circumferential head flange
306 ovoid member
3130 aperture
3132 base panel
3134 neck
3136 head
3138 circumferential head flange It is to be noted that, for convenience, the last positions of the reference numerals of alternative embodiments of the invention duplicate those of the numerals of the embodiment of FIGS. 1–7, where reference is made to similar or corresponding parts. However, it should not be concluded merely from this numbering convention that similarly numbered parts are equivalents.

DETAILED DESCRIPTION OF THE INVENTION

As shown in FIG. 1, the device, apparatus or garment 1 for releasably securing condoms appears to look like a normal female panty when worn by a user 4. However, there is a releasable flap 2 at the crotch area and a sewn-on pocket 3 near the waist area. The pocket is capable of holding a prepackaged mount of lubricant which can be applied to the penis immediately before intercourse, thereby allowing easier insertion into the vagina.

Figure 2:
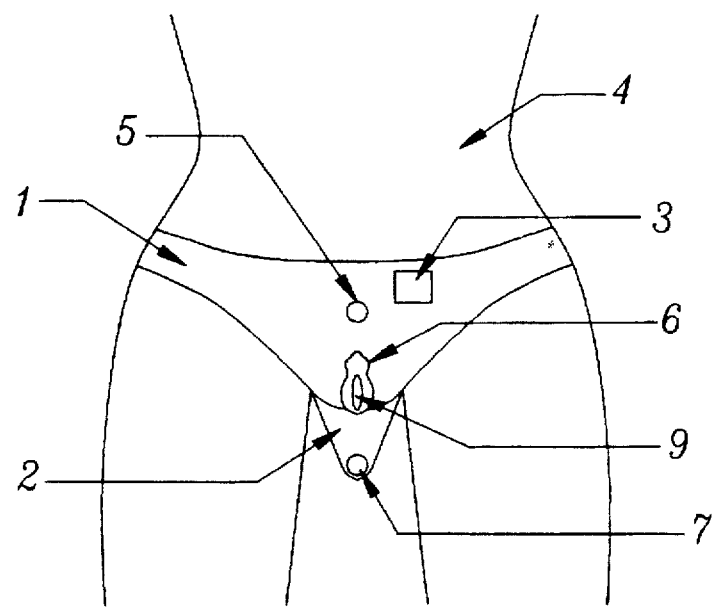
FIG. 2 is a front view of the garment of FIG. 1 in a second position wherein the crotch flap is released.

FIG. 2 shows the garment 1 of the present invention with the flap 2 in an open position, revealing a resilient plastic ovoid (oval-shaped) condom attachment member 6 which is sewn or otherwise permanently attached within or around an opening 9 in the fabric crotch area of the garment 1. Hook and loop fasteners 5 and 7 keep the flap 2 closed.

Figure 3:
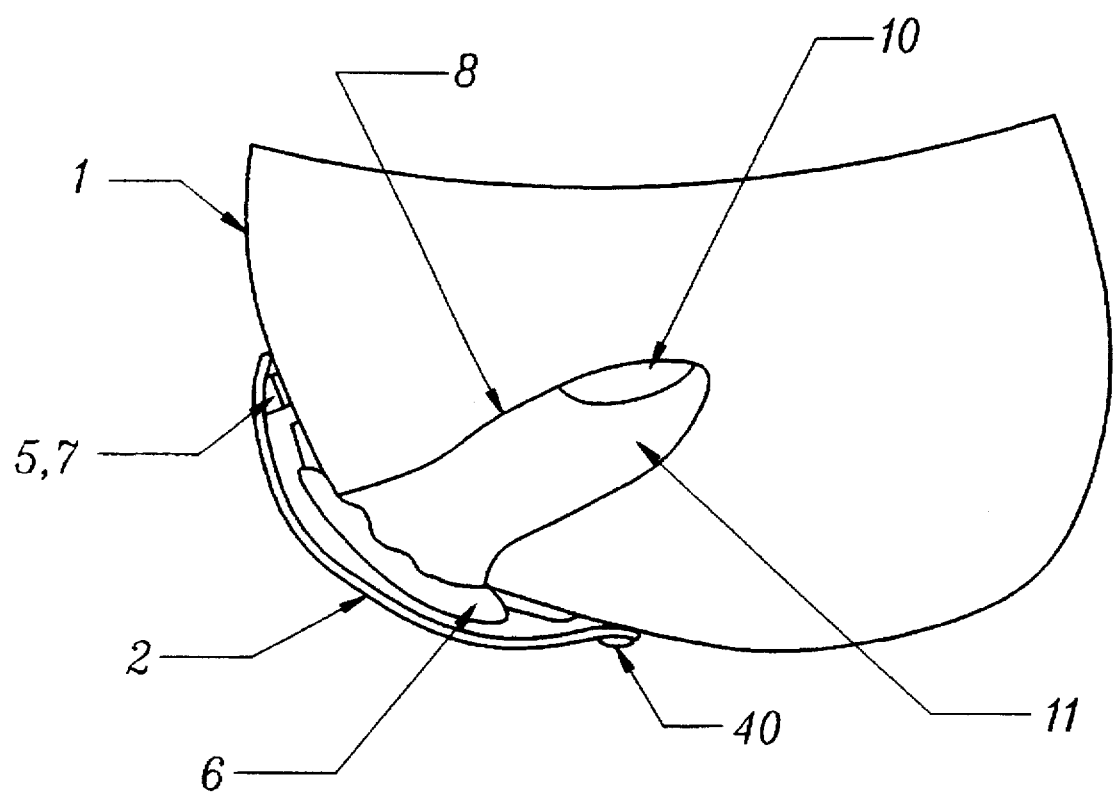
FIG. 3 is a sectional side view of the garment of FIG. 1 with a female condom in place.

FIG. 3 shows a side sectional elevation of the garment 1 assembled together with a female condom 8. Female condom 8 is shown as it appears when inserted into a vagina. A flee-floating lower inner positioning ring 10 holds the lower end of the condom 8 in place in a fashion similar to that by which a woman's diaphragm-type contraception device is held in place. The latex condom 8 is thin and disposable and has a film tube 11 of a thickness similar to that of a typical male condom.

Commonly available fabric snaps 40 are shown in FIG. 3. These allow the entire flap 2 to be removed if so desired. Alternatively, hook and loop fasteners could be used at both the top and bottom of the flap, or the flap could be permanently sewn in place.

Figure 4:
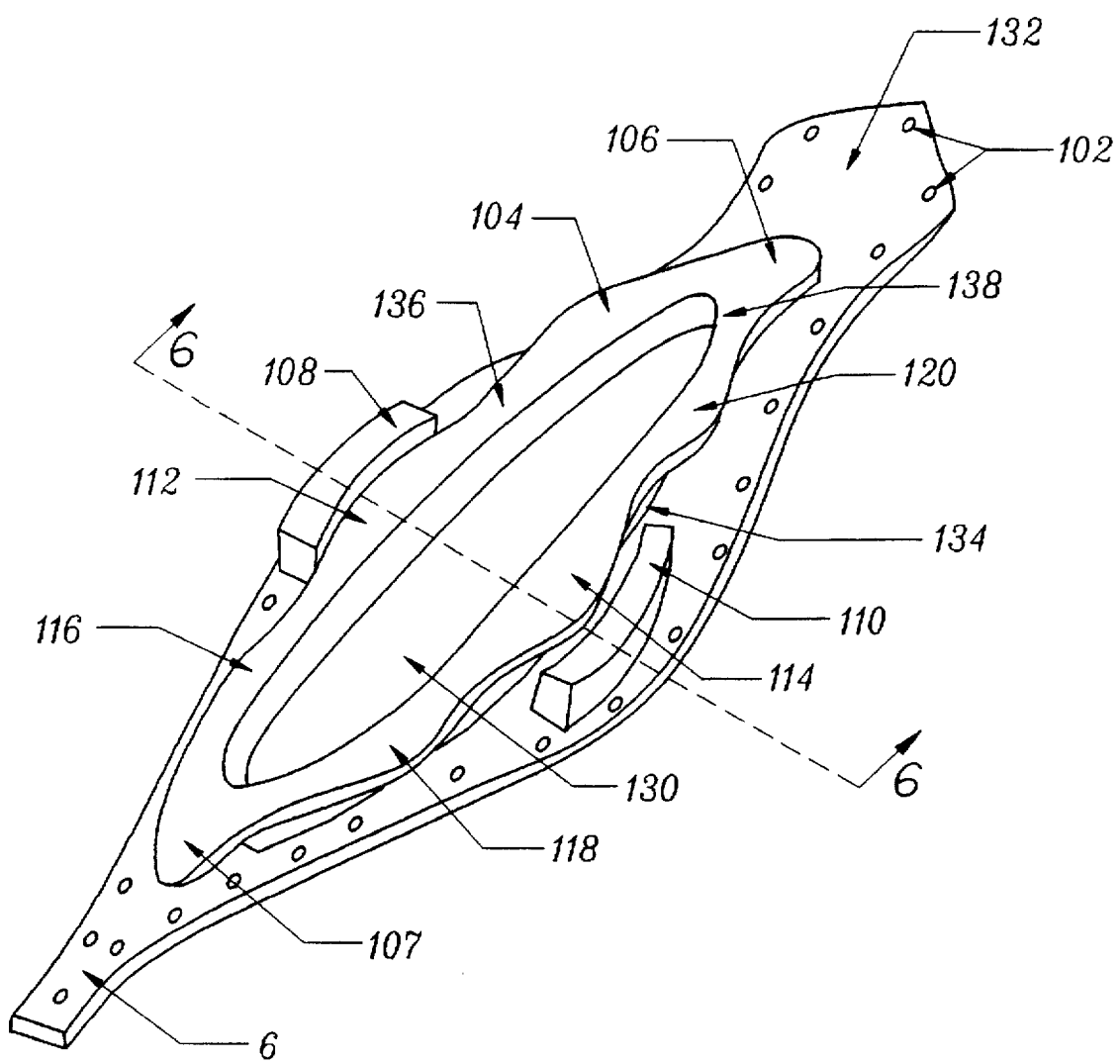
FIG. 4 is a perspective view of a preferred, or first, embodiment of the ovoid condom attachment member of the garment of FIG. 1.
Figure 6:
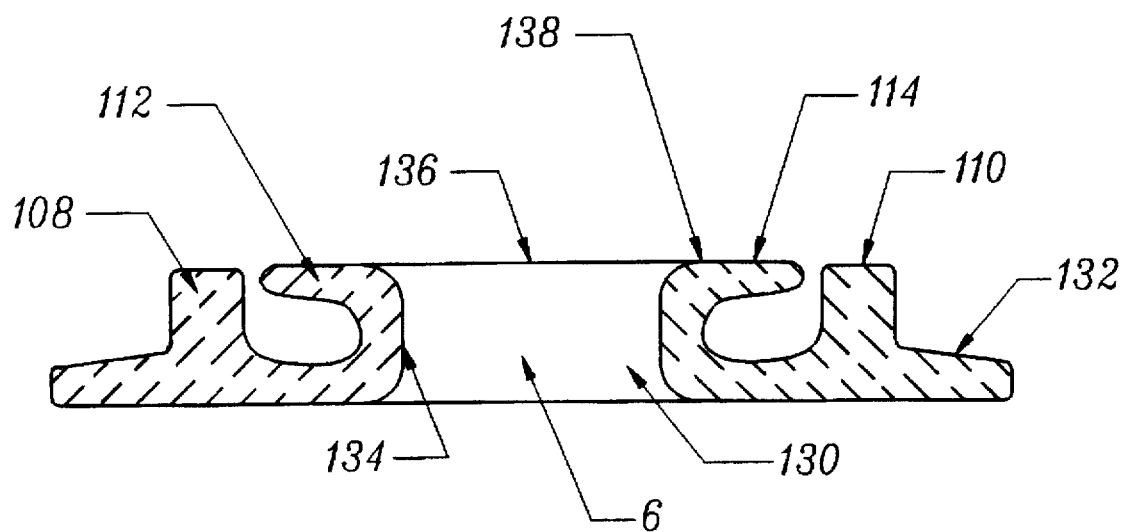
FIG. 6 is a sectional from view of the ovoid attachment member of FIG. 4, taken along line 6—6 of FIG. 4.

FIG. 4 shows a perspective view of a preferred resilient molded-plastic female condom attachment member 6. This ovoid member 6 is roughly annular, forming a slit-shaped oval aperture 130 that conforms in shape to a woman's external vaginal opening. Holes 102 in the base panel 132 of the condom attachment member 6 may be used to sew the member onto the fabric of the crotch of the garment 1. Alternatively, the base panel may be glued or heat-sealed in place. FIG. 6 shows a cross-sectional elevation of the member 6 of FIG. 4.

Rising up from the base panel 132 is an enlarged protruding head 136 formed atop an intermediate narrow side wall or annular neck 134. A circumferential head flange 138 projects radially outward laterally (with respect to the column of the annular neck) on the head 136, which head and neck form and surround the central slit-like aperture 130 of the ovoid member 6. Horizontally disposed and radially projecting resilient tabs or flange protuberances 104, 106, 107, 112, 114, 116, 118 and 120 vary the effective width of the head flange 138 and help to clasp the fixed rim ring 122 of the female condom 8 in place, as discussed below. The head 136 comprises the circumferential head flange and flange protuberances.

The flange protuberances also aid in the installation of the female condom 8, i.e., once the condom rim ring 122 is stretched over the top protuberance 106 and bottom protuberance 107, stretching it over the remainder of the head flange is facilitated by the undulating circumference thereof.

Figure 5:
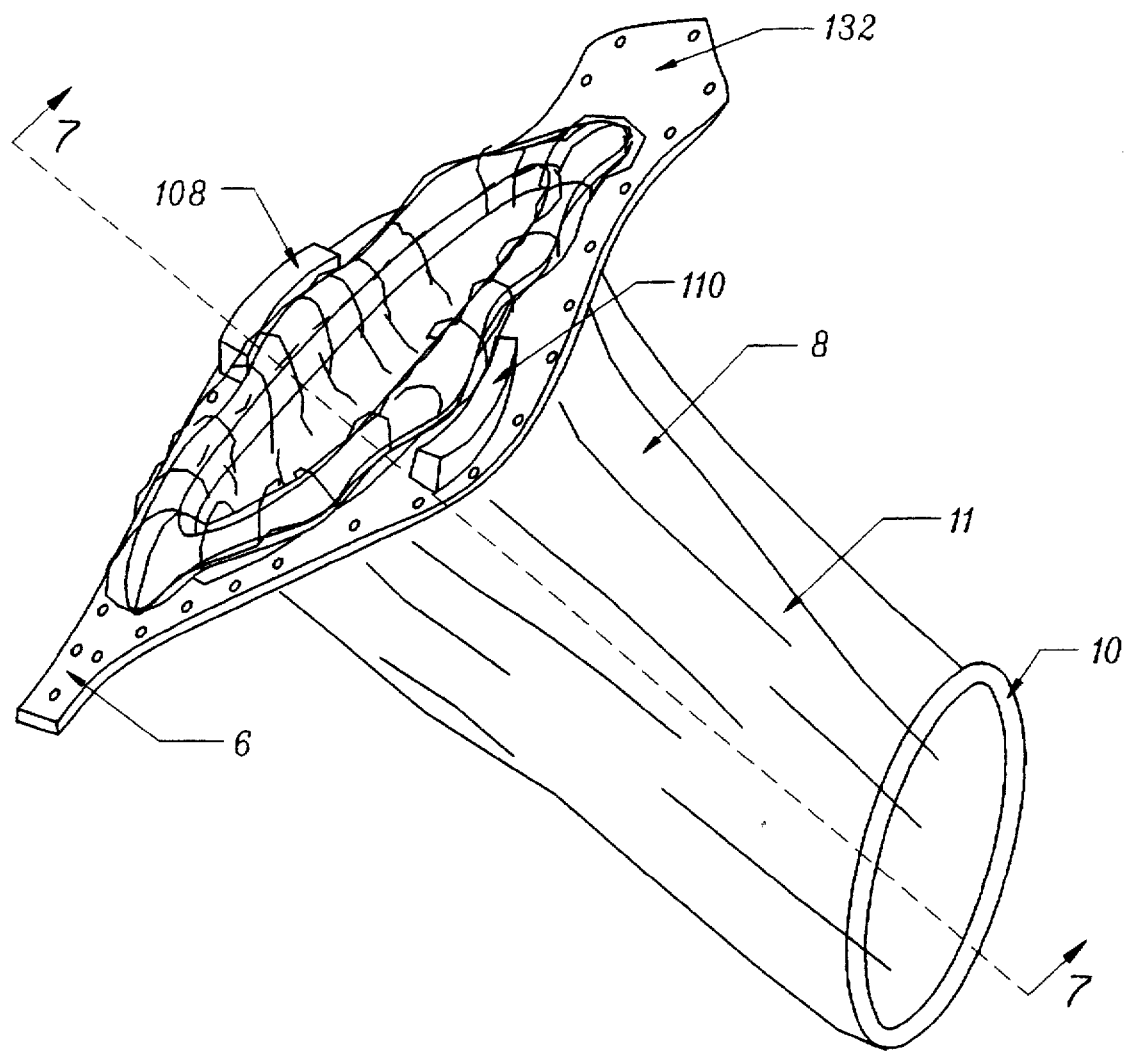
FIG. 5 is a perspective view of the ovoid attachment member of FIG. 4 with a female condom locked in place thereon.
Figure 7:
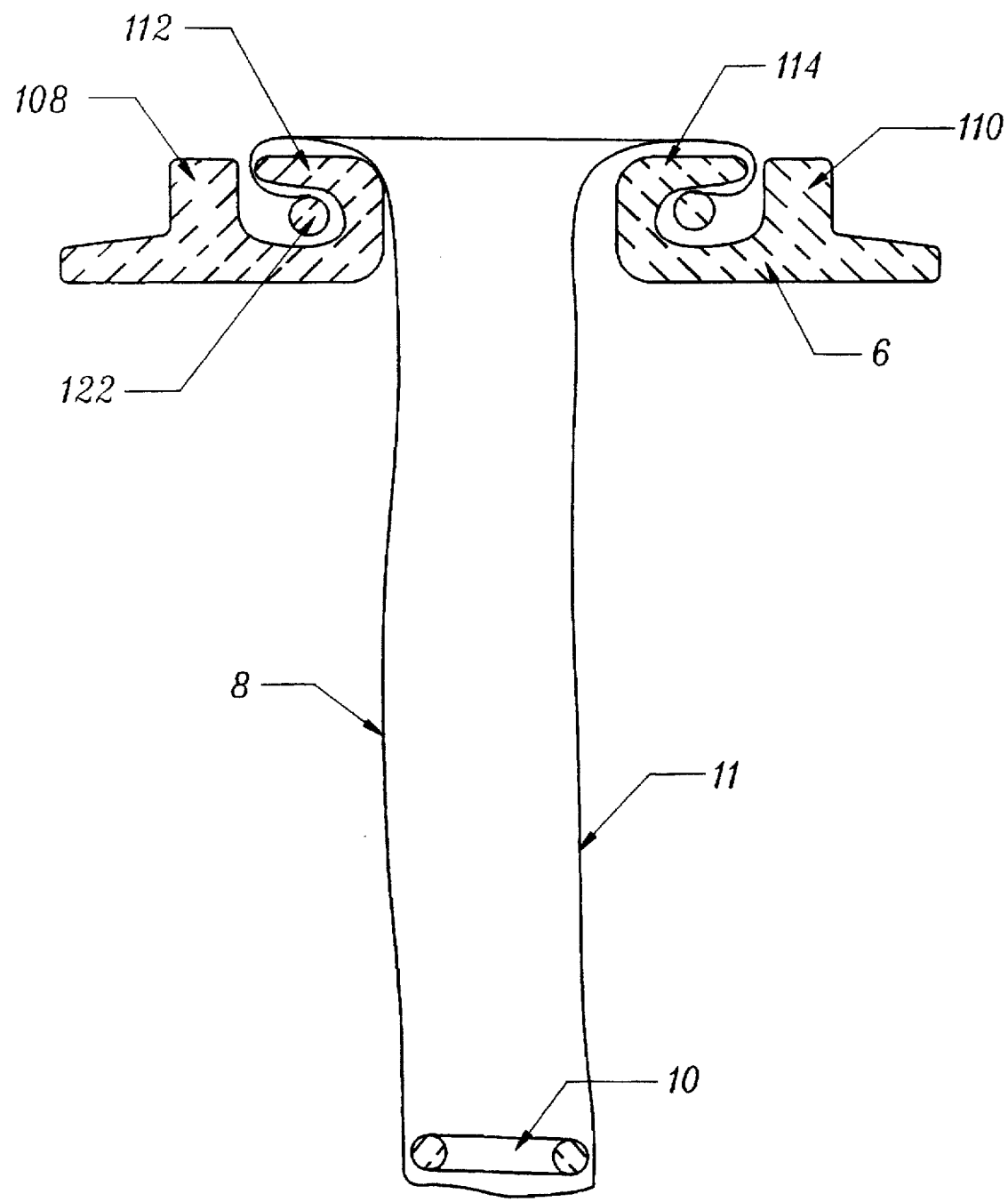
FIG. 7 is a sectional front view of the ovoid attachment member of FIG. 4, showing a female condom secured in place thereon, taken along line 7—7 of FIG. 5.

FIGS. 5 and 7 show a female condom 8 secured in place on the soft plastic member 6. Fixed at the upper end of the condom, as an extension of the film tube 11 thereof, is the outer condom rim ring 122, which is a standard rolled-latex design that will fit securely in the recess created between protuberances 112, 114 and the centrally opposed retaining bars 108, 110. The bars protrude up from the base panel 132 and are diametrically opposed to one another on two sides of the neck 134. They are situated closely adjacent to the neck so as to be able to capture the condom rim ring 122 between themselves and the neck.

Means thereby are included for securing the elastic upper rim ring 122 of the female condom 8, such as the REALITY brand female condom, to the narrowed neck 134 of the attachment member 6. In the preferred embodiment, the securing means comprises the radially enlarged circumferential head flange 138, the protuberances 104, 106, 107, 112, 114, 116, 118, 120, and the retaining bars 108 and 110.

In the embodiment of FIGS. 1–7, the film tube 11 of the female condom 8 is inserted into the vaginal opening of the wearer 4 and retained therein by its free inner positioning ring 10. The fixed outer rim ring 122 of the condom then is threaded through the center aperture 130 of the ovoid member 6 and stretched over the upper circumferential head flange 138 of the head 136 of the ovoid member 6. The rim ring of the female condom then snaps back under the circumferential head flange and rests in the reduced-diameter groove forming the neck 134.

Figure 8:
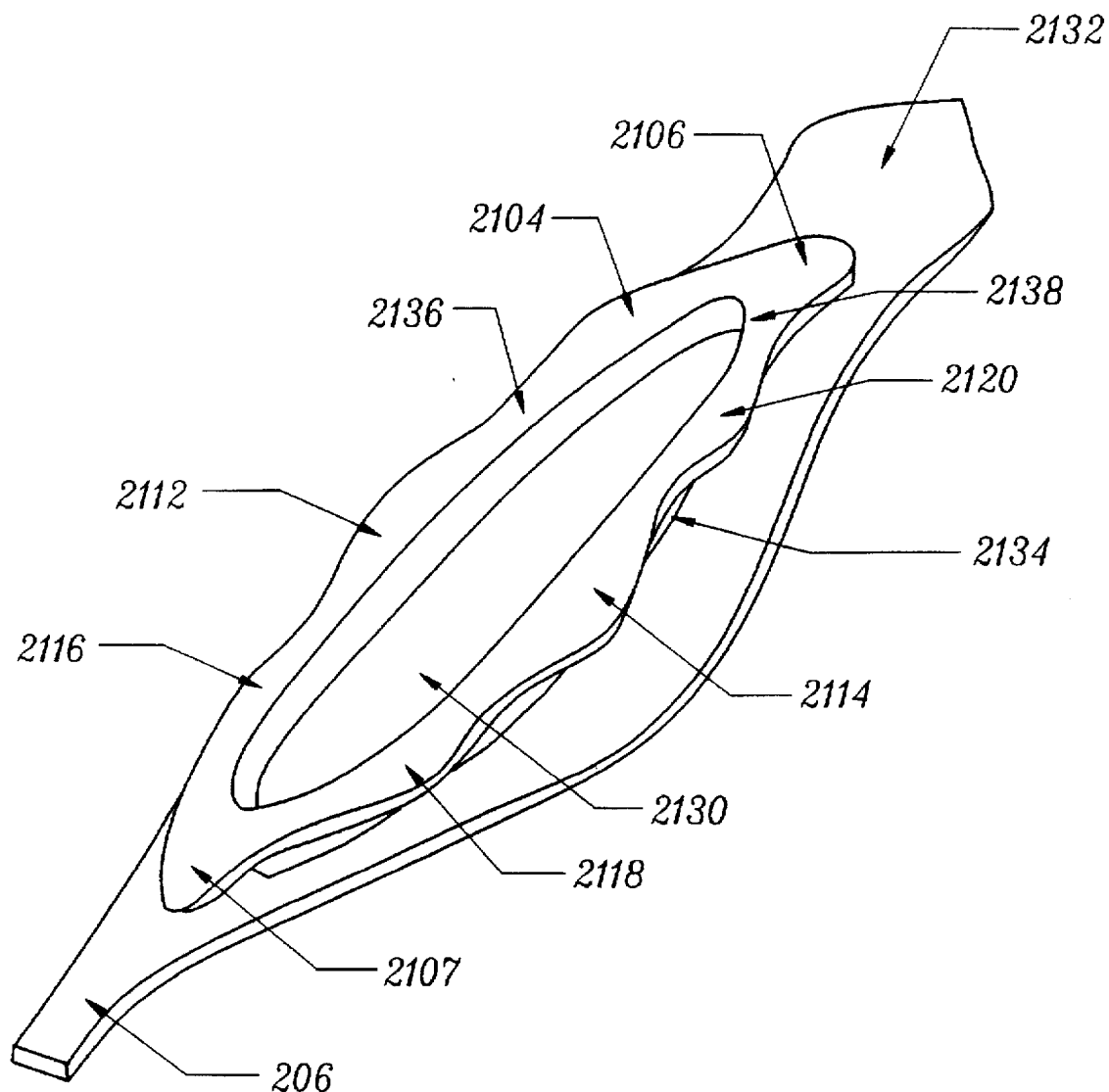
FIG. 8 is a perspective view of an alternate, or second, embodiment of the ovoid attachment member of the female condom securing device of the present invention.

FIG. 8 is a perspective view of an alternate embodiment of a resilient molded-plastic female condom attachment member 206 which eliminates the retaining bars. This version may not be quite as secure as the preferred embodiment, but still will work effectively.

The ovoid member 206 is annular, forming a slit-like oval aperture 2130. Holes (not illustrated) in the base panel 2132 of the condom attachment member 206 may be used to sew the member onto the fabric of the crotch of the garment 1 of FIGS. 1–3. Rising up from the base panel 2132 is a protruding head 2136 formed atop an intermediate narrow neck 2134. A circumferential head flange 2138 projects radially outward laterally (with respect to the column of the annular neck) on the head 2136, which head forms and surrounds the aperture 2130. Flange protuberances 2104, 2106, 2107, 2112, 2114, 2116, 2118 and 2120 vary the effective width of the head flange 2138. The head 2136 comprises the circumferential head flange and its protuberances.

In this embodiment, the condom rim ring securing means comprises the radially enlarged circumferential head flange 2138 together with the width-varying flange protuberances, both acting in cooperation with the narrow neck 2134 (retaining bars being absent).

Figure 9:
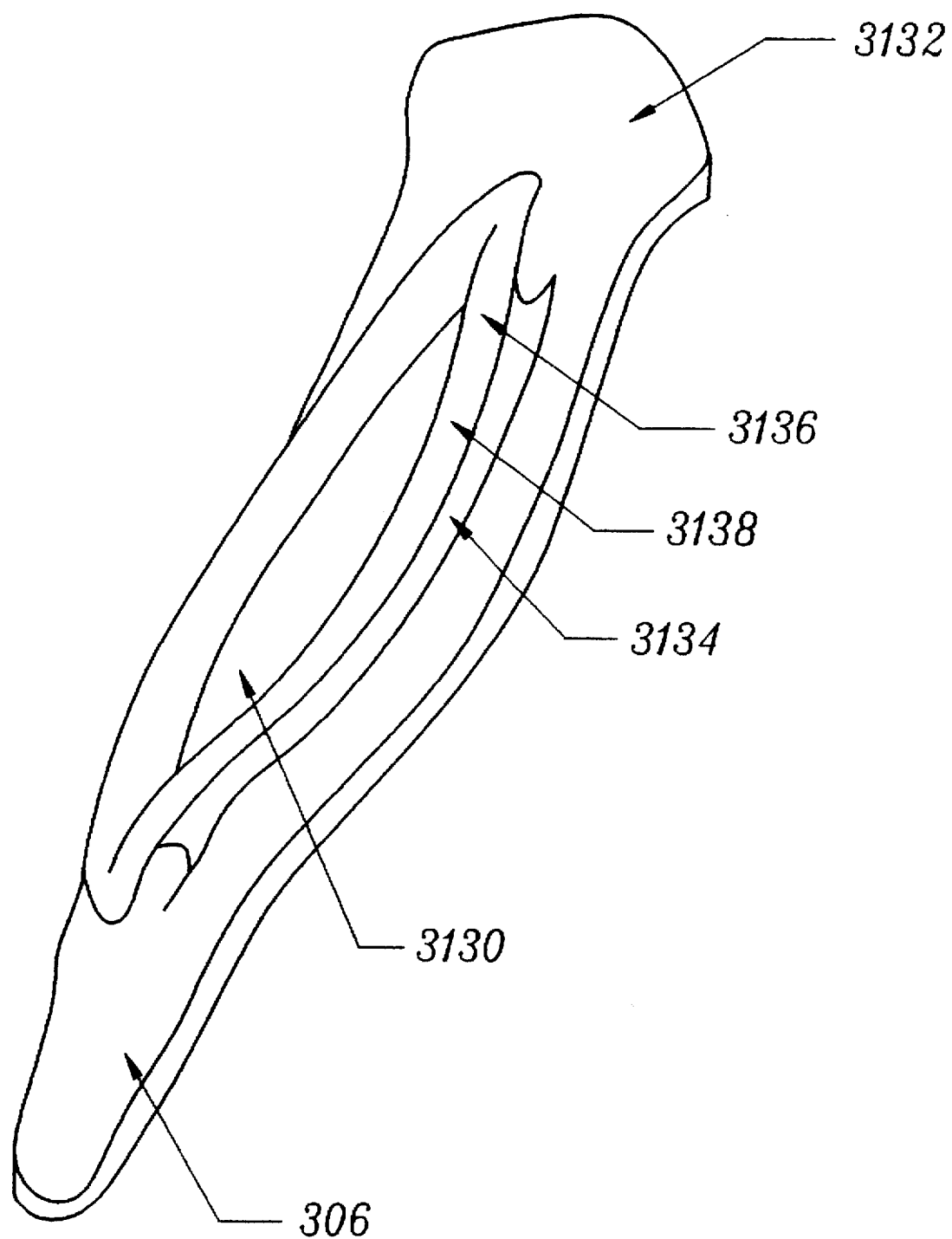
FIG. 9 is a perspective view of an alternate, or third, embodiment of the ovoid attachment member of the device of the present invention.

FIG. 9 is a perspective view of another alternate, or third, embodiment of an ovoid condom attachment member 306. In this embodiment, eliminated are both the retaining bars and the protuberances which vary the width of the circumferential head flange.

The ovoid member 306 is annular, forming a slit-like oval aperture 3130. Holes (not illustrated) in the base panel 3132 of the attachment member 306, or other known means, may be used to attach the member onto the fabric of the crotch of the garment 1 of FIGS. 1–3. Rising up from the base panel 3132 is a protruding enlarged head 3136 formed atop an intermediate narrow neck 3134. A circumferential head flange 3138 projects radially outward laterally on the head 3136, which head forms and surrounds the slit aperture 3130. The head flange 3138 extends radially outward at a more or less constant width. The head 3136 simply comprises the head flange 3138.

In this embodiment, the condom rim ring securing means comprises the radially enlarged circumferential head flange 3138 acting in cooperation with the narrow neck 3134 (retaining bars and width-varying flange protuberances being absent).

The above disclosure is sufficient to enable one of ordinary skill in the art to practice the invention, and provides the best mode of practicing the invention presently contemplated by the inventor. While there is provided herein a full and complete disclosure of the preferred embodiments of this invention, various modifications, alternative constructions, and equivalents may be employed without departing from the true spirit and scope of the invention. Such changes might involve alternative materials, components, structural arrangements, sizes, operational features or the like. Therefore, the above description and illustrations should not be construed as limiting the scope of the invention, which is defined by the appended claims.

What is claimed is:

1. Garment apparatus for releasably securing female condoms including:
   a panty made of breathable material, the panty having a crotch, the crotch having an opening; and
   a resilient ovoid condom attachment member affixed to the panty at the crotch opening, the ovoid member having
   a base panel;
   an annular ovoid neck protruding up from the base panel; and
   a circumferential head flange on an upper end of the neck projecting radially outward laterally from the neck, the neck and head flange forming a central slit-shaped aperture, the aperture communicating with the opening.

2. The apparatus of claim 1 wherein:
   the panty material is cloth fabric, the ovoid member is plastic, and the ovoid member is sewn onto the crotch.

3. The apparatus of claim 2 further including:
   a plurality of horizontally disposed resilient flange protuberances radially projecting from the head flange, which protuberances vary the width of the head flange.

4. The apparatus of claim 2 further including:
   at least one retaining bar protruding up from the base panel, the retaining bar disposed radially outward of the neck and closely adjacent thereto.

5. The apparatus of claim 4 wherein:

there are a pair of retaining bars, the retaining bars being diametrically opposed on opposite sides of the neck.

6. Garment apparatus for releasably securing female condoms including:

a panty having a crotch, the crotch having an opening; and a resilient ovoid condom attachment member fixed to the panty at the crotch opening, the ovoid member having
- a base panel;
- an annular ovoid neck protruding up from the base panel;
- a circumferential head flange on the neck projecting radially outward laterally from the neck, the neck and head flange forming a central slit-shaped aperture, the aperture communicating with the opening; and
- a plurality of horizontally disposed resilient flange protuberances radially projecting from the head flange, which protuberances vary the width of the head flange.

7. The apparatus of claim 6 wherein:

the panty is made of breathable fabric, and further including
- a releasable cloth flap portion on the crotch, which flap covers the ovoid member.

8. The apparatus of claim 7 further including:

hook and loop type fasteners securing a top of the flap to the panty.

9. The apparatus of claim 8 further including:

at least one pocket affixed to the panty.

10. Garment apparatus for releasably securing female condoms including:

a panty having a crotch, the crotch having an opening; and a resilient ovoid condom attachment member fixed to the panty at the crotch opening, the ovoid member having
- a base panel;
- an annular ovoid neck protruding up from the base panel;
- a circumferential head flange on the neck projecting radially outward laterally from the neck, the neck and head flange forming a central slit-shaped aperture, the aperture communicating with the opening; and
- at least one retaining bar protruding up from the base panel, the retaining bar disposed radially outward of the neck closely adjacent thereto.

11. The apparatus of claim 10 wherein:

there are a pair of retaining bars, the retaining bars being diametrically opposed.

12. The apparatus of claim 11 further including:

a plurality of horizontally disposed resilient flange protuberances radially projecting from the head flange, which protuberances vary the width of the head flange.

13. The apparatus of claim 12 wherein:

the panty is made of breathable fabric, and further including
- a releasable cloth flap portion on the crotch, which flap covers the ovoid member.

14. The apparatus of claim 13 further including:

hook and loop type fasteners securing a top of the flap to the panty.

15. The apparatus of claim 14 further including:

at least one pocket affixed to the panty.

* * * * *